(12) United States Patent
Osadchy et al.

(10) Patent No.: US 6,370,411 B1
(45) Date of Patent: Apr. 9, 2002

(54) CATHETER CALIBRATION

(75) Inventors: Daniel Osadchy, Haifa; Avraham Matcovitch, Nesher, both of (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/402,775

(22) PCT Filed: Feb. 10, 1998

(86) PCT No.: PCT/IL98/00064

§ 371 Date: Dec. 27, 1999

§ 102(e) Date: Dec. 27, 1999

(87) PCT Pub. No.: WO99/40856

PCT Pub. Date: Aug. 19, 1999

(51) Int. Cl.[7] .................................................. A61N 1/05
(52) U.S. Cl. ........................ 600/372; 600/373; 607/115
(58) Field of Search ................................ 600/372, 373, 600/377; 607/115, 116

(56) References Cited

U.S. PATENT DOCUMENTS

| | | |
|---|---|---|
| 3,644,825 A | 2/1972 | Davis, Jr. et al. |
| 3,868,565 A | 2/1975 | Kuipers |
| 4,017,858 A | 4/1977 | Kuipers |
| 4,054,881 A | 10/1977 | Raab |
| 4,580,557 A | 4/1986 | Hertzmann |
| 4,849,692 A | 7/1989 | Blood |
| 5,042,486 A | 8/1991 | Pfeiler et al. |
| 5,211,165 A | 5/1993 | Dumoulin et al. |
| 5,318,025 A | 6/1994 | Dumoulin et al. |
| 5,377,678 A | 1/1995 | Dumoulin et al. |
| 5,383,874 A | 1/1995 | Jackson et al. |
| 5,391,199 A | 2/1995 | Ben-Haim |
| 5,441,520 A * | 8/1995 | Olsen et al. ............... 607/6 |
| 5,445,150 A | 8/1995 | Dumoulin et al. |
| 5,617,857 A | 4/1997 | Chader et al. |
| 5,800,350 A * | 9/1998 | Coppleson et al. ......... 600/372 |
| 5,813,404 A * | 9/1998 | Devlin et al. ............... 128/639 |
| 5,904,651 A * | 5/1999 | Swanson et al. ............ 600/407 |

* cited by examiner

*Primary Examiner*—Carl Layno
(74) *Attorney, Agent, or Firm*—Louis J. Capezzuto

(57) ABSTRACT

A probe assembly (18) for connection to a console (34) including a problem (20) for insertion into the body of a subject and a cable (21) for connecting the problem (20) to the console (34), the problem (20) having distal (22) and proximal ends and including a microcircuit (90) which stores information relating to the probe (20), and the cable (21) including access circuitry for accessing the microcircuit in the probe.

42 Claims, 3 Drawing Sheets

US 6,370,411 B1

CATHETER CALIBRATION

RELATED APPLICATIONS

This application is related to PCT patent application PCT/IL97/00060, which is incorporated herein by reference.

FIELD OF THE INVENTION

The present invention relates generally to systems for medical diagnosis and treatment, and specifically to medical catheters whose location can be detected.

BACKGROUND OF THE INVENTION

Various methods and devices have been described for determining the position of a probe or catheter tip inside the body using electromagnetic fields, such as in U.S. Pat. No. 5,042,486 and PCT patent publication WO 94/04938, whose disclosures are incorporated herein by reference. Other electromagnetic tracking systems, not necessarily for medical applications, are described in U.S. Pat. Nos. 3,644,825, 3,868,565, 4,017,858, 4,054,881 and 4,849,692, whose disclosures are likewise incorporated herein by reference.

U.S. Pat. No. 5,391,199, whose disclosure is incorporated herein by reference, describes a system that incorporates a catheter, which includes a position measuring device that can determine the position of the catheter in three dimensions, but not its orientation.

PCT patent application PCT/WO96/05768, which is assigned to the assignee of the present patent application and whose disclosure is likewise incorporated herein by reference, describes a catheter system including means for determining the six-dimensions of position and orientation of the catheter's distal tip. This system uses a position sensor, formed of a plurality of non-concentric coils, adjacent to a locatable site in the catheter, for example near its distal tip. Preferably three orthogonal coils are used. These coils generate signals in response to externally applied magnetic fields, which allow for the computation of six position and orientation coordinates, so that the position and orientation of the catheter are known without the need for imaging the catheter.

U.S. Pat. No. 4,580,557 describes a surgical laser system for connection to various peripheral surgical devices. The system identifies to which device it is connected according to characteristics of a signature resistor embedded within the device. The resistor uniquely identifies the device in which it is embedded.

U.S. Pat. No. 5,383,874 describes a system for identifying and monitoring catheters, including identification means carried within the handle of the catheter body. In one embodiment of the catheter in this patent, the handle includes a solid-state microchip pre-programmed with a digital value representing an identification code and other operational and functional characteristics of the catheter. The handle is connected by a cable to a control console, which receives data from the microchip. In one disclosed embodiment, the microchip may record the number of times the catheter has been used.

U.S. Pat. No. 5,617,857 describes an imaging system which determines the location of a medical instrument. A read-only storage device is positioned on or in the medical instrument for storing initialization information characteristic of the instrument. Thus, the system may determine the type of the instrument connected thereto, and receive initialization information associated with the instrument type. This patent further suggests preventing use of the instrument unless the initialization information was transferred from the storage device to the imaging system. A verification method is also described in which the initialization information is verified for correctness. Two alternatives are suggested for the location of the storage device. One alternative suggests embedding the device directly in the instrument. A second alternative suggests embedding the storage device within an attachment, essentially an instrument handle, to which a certain type of instrument may be fit.

Thus, in some of the embodiments described in the above-referenced patents, information regarding a catheter (or other medical tool) is stored in an attachment to the catheter and not in the catheter itself. These embodiments are not suitable for storing item-specific information such as calibration information.

In other embodiments of the above-referenced patents, information is stored in the catheter. These embodiments, however, suffer from over-complexity, requiring for example multiple digital signal wires to run along the catheter. This complexity is not feasible for mass use in disposable catheters.

SUMMARY OF THE INVENTION

It is an object of some aspects of the present invention to provide means for convenient electronic storage and recall of calibration information regarding a catheter.

It is another object of some aspects of the present invention to provide means for convenient electronic storage and recall of calibration information regarding a catheter, in which the recall time of the information is minimal.

It is another object of some aspects of the present invention to provide means for providing improved communication between the catheter and a control console.

It is a further object of some aspects of the present invention to provide catheters of minimal cost and complexity, which are capable of storing and recalling calibration information.

In one aspect of the present invention, a catheter assembly for connection to a control console comprises two parts: a catheter of minimal complexity which is inserted into a patient's body, and a connection cable which connects between the proximal end of the catheter and the console. The catheter comprises a microcircuit which carries substantially only information specific to the catheter, which is not in common with other catheters of the same model. Such information includes, for example, item-specific calibration data and a date of first use of the catheter. The cable comprises an access circuit which receives the information from the catheter and passes it in a suitable form to the console.

Preferably, the cable operates with all catheters of a specific model or type, and therefore when a catheter is replaced, there is no need to replace the cable. Particularly, catheters which are planned for one-time use do not require replacement of the cable, which does not come in contact with patients.

In a preferred embodiments of the present invention, the access circuit verifies that the catheter is of the model which is compatible with the cable. Preferably, the connection between the catheter and the cable is unique for each catheter model. Alternatively or additionally, the model identification is stored in the microcircuit and the access circuit verifies that the model identification is the same in the cable and the catheter.

In some preferred embodiments of the present invention, each cable is associated with a few catheters models, and the model identification stored in the microcircuit is used by the access circuitry to identify which catheter model is in use.

In some preferred embodiments of the present invention, the catheter microcircuit contains data which is stored digitally. Preferably, the leads of the microcircuit are coupled directly to sockets in a receptacle at the distal end of the cable. Thus, the catheter does not contain digital signal wires, and still allows quick access to the information in the microcircuit. Also, digital electronic signals transmitted from the microcircuit to the console via the cable do not interfere with low-level analog signals conveyed by wires from the distal end of the catheter to the cable. Preferably, the access circuit is located within the receptacle at the distal end of the cable and includes the socket which receives the leads of the microcircuit.

In preferred embodiments of the present invention, the microcircuit stores minimal calibration and/or initialization information regarding the catheter. Alternatively or additionally, the microcircuit stores usage information regarding the catheter, such as the date of first use of the catheter.

In preferred embodiments of the present invention, the catheter comprises at its proximal end a handle which contains controls which are used to manipulate the catheter. It is noted that in catheters in which the handle is not at the proximal end of the catheter, the length beyond the handle does not add to the functionally of the catheter but raises the cost of the catheter and of sterilization thereof. Preferably, the catheter microcircuit is contained in the handle. Alternatively, the handle is separate from the catheter, and is rather fixed at the distal end of the cable, and the microcircuit is contained within a connector at the proximal end of the catheter, which connects to the handle.

In some preferred embodiments of the present invention, the catheter includes coils which generate analog signals indicative of the position of the catheter, as described, for example, in the above-reference PCT/WO96/05768 patent application. The cable preferably comprises amplifiers which are used to amplify the analog signals. Alternatively or additionally, the amplifiers may be used to amplify other signals, such as physiological measurements. Preferably, the amplifiers are within the receptacle so that they are as close as possible to the coils and/or the other sources of signals. It is noted that placing the amplifiers within the console is not desirable due to interference from circuitry of the console which generates noise in neighboring wires and due to noise pickup over the long distance between the distal end of the catheter and the console. The signals generated within the catheter are relatively weak and must be protected from attenuation and noise. Placing the amplifiers in the catheter adds to the complexity and cost of the catheter, which is also undesirable.

In some of these preferred embodiments, the access circuitry includes one or more analog-to-digital (A/D) converter circuits, which converts analog signals from the catheter into a digital form, which is conveyed to the console. Thus, the attenuation and noise problems mentioned above are substantially eliminated.

In other preferred embodiments of the present invention, the catheter itself includes the one or more analog-to-digital (A/D) converter circuits. In these embodiments, the access circuit couples only digital signals from the catheter to the console. In one such preferred embodiment, an A/D converter is adjacent to the distal tip of the catheter.

In some preferred embodiments of the present invention, the cable comprises an additional microcircuit in which information characteristic of the one or more models of catheters associated with the cable, is stored. Such information may include, for example, the configuration of the catheters and usage codes. Preferably, the additional microcircuit also includes calibration information for the access circuit and the amplifiers within the cable. The calibration information of the amplifiers may include, for example, their zero-gain, DC offset and linearity. Thus, information which does not have to be in the catheter is stored in the cable, and the catheter is less complex and costly. Preferably, the console substantially does not require any other catheter-specific information beyond that supplied by the microcircuits in the catheter and, preferably, the cable, so that newer models of catheters may be used with the console without updating software or hardware of the console.

Preferably, the microcircuits comprise a read/write memory component, such as an EEPROM, EPROM, PROM, Flash ROM or non-volatile RAM, and the information is stored in digital form. Alternatively or additionally, either of the microcircuits may comprise a read-only memory which is pre-programmed at the time of manufacture.

In preferred embodiments of the present invention, the calibration information includes data relating to the relative displacement of the distal tip of the catheter from the coils. In some other preferred embodiments of the present invention, the calibration information also includes data relating to deviation of the coils from orthogonality, or data relating to the respective gains of the coils, or a combination of these data. The above calibration information generally varies from one catheter to the other and therefore is preferably stored in the microcircuit within the catheter. Preferably, the data is determined in a calibration method, such as described in PCT/IL97/00060. Other calibration information may include the general configuration of the catheter and the gain and offset of the access circuitry, and is preferably stored in the microcircuit in the cable.

In some preferred embodiments of the present invention, the catheter is electrically isolated from signal processing and computing apparatus in the console, and the calibration information includes data relating to isolation circuitry in the catheter. Preferably, the catheter is isolated by at least one inductive element, such as an isolation transformer, adjacent to the proximal end of the catheter or in the catheter handle. Alternatively, the catheter may be isolated by one or more opto-isolators, or other types of isolation circuitry known in the art. Such inductive elements and other isolation circuitry typically introduce non-linearities in signals conveyed thereby. Such non-linearities may lead to significant distortions particularly in analog signals conveyed by wires from the distal end of the catheter to the signal processing circuits. Therefore, the calibration information preferably includes data relating to signal non-linearities introduced by the inductive elements and/or other isolation circuitry.

The calibration data may be recorded in the microcircuit in the catheter in the form of lookup tables, polynomial coefficients or any other suitable form known in the art.

In preferred embodiments of the present invention, calibration data are produced and recorded at or close to the time of manufacture, and the microcircuits are configured so as to prevent subsequent recording of calibration data by a user. For example, when the microcircuit comprises an EPROM or PROM, a suitable programming device connects to the catheter connector and programs the EPROM or PROM by inputting digital signals thereto through the connector from a computer used in calibration. Thereafter, the EPROM or PROM may not be re-programmed.

In other such preferred embodiments wherein the microcircuit comprises an EEPROM or non-volatile RAM device, the EEPROM or non-volatile RAM device includes a write-enable input connection, of a type known in the art, which is connected to a write-enable pin in the connector at the proximal end of the catheter. At the time of calibration, the write-enable input is enabled, and calibration data are recorded in the microcircuit. Thereafter the write-enable input is disabled, for example by removing the write-enable pin or by connecting it to electrical ground, so that further calibration data may not be recorded in the microcircuit.

Alternatively, in preferred embodiments of the present invention wherein the microcircuit comprises an EEPROM device, the write-enable input may be disabled by sending a write-protect command to the device. This command may be reversible or irreversible.

In still other preferred embodiments of the present invention, the microcircuit in the catheter and/or the microcircuit in the cable comprise access control circuitry, such as, for example, the X76F041 Password Access Security Supervisor (PASS™) SecureFlash ROM device, manufactured by Xicor, Inc. The microcircuit is preferably programmed with a password, so that after calibration data are produced and recorded at the time of manufacture, further calibration data may not be recorded in the microcircuit, with the possible exception of data recording by factory-authorized personnel to whom the password is known.

In some preferred embodiments of the present invention, data recorded in the microcircuit include a calibration code, which is encrypted in accordance with methods known in the art, so as to ensure that calibration data have not been altered or corrupted. When a user connects the catheter to a suitable console, which console comprises a computer, the computer reads the calibration code and compares the code with pre-programmed values. If the code does not match the desired pre-programmed value, the computer causes a message to be displayed indicating that the catheter may not be appropriately calibrated. The computer may prevent further operation until a catheter having a code matching the desired pre-programmed value is connected thereto.

Preferably the calibration code is encrypted using a method that prevents decryption by unauthorized parties, for example the RSA encryption scheme, using a public key and a private key, or other methods known in the art. When a method such as RSA encryption is used, the private key is known only to authorized manufacturers of the catheter, so as to prevent the possible use of unauthorized substitutes of possibly inferior quality.

In further preferred embodiments of the present invention, data recorded in the microcircuit include an expiration date and time, after which the catheter may not be used. When a user connects the catheter to a suitable console, which console comprises a computer, the computer reads the expiration date and time and compares them to the actual date and time, generated, for example, by a real-time clock circuit. If the expiration date and time have passed, the computer caused a message to be displayed indicating that the catheter is unsuitable for further use. The computer may prevent further operation until a catheter having a valid expiration date and time is connected thereto.

Preferably the expiration date and time are recorded by the console computer by programming the microcircuit in the catheter when the catheter is first used. Thus, when the catheter is connected to a console for the first time, the computer detects that no expiration date and time have yet been recorded in the microcircuit, and programs the microcircuit with the appropriate expiration data and time, at a pre-set interval after the actual date and time. Preferably, the pre-set interval is stored within the cable and is determined by the manufacturer, based on the expected useful life of the catheter.

In a preferred embodiment in which the microcircuit comprises access control circuitry, the microcircuit is programmed so that a memory location therein is operable in a "read access and program only" mode. The mode may be changed only by entry of an appropriate password, which is generally not available to users of the catheter. In the "read access and program only" mode, a number stored in the memory location may be decreased, by changing a bit from "1" to "0", but not increased, since the microcircuit as programmed will not permit a "0" to be changed to a "1". Preferably the memory location is set at the time of manufacture to contain a maximum value, i.e., all bits set to "1". Then, as described above, at the time of first use, the computer programs the microcircuit with the appropriate expiration time and date by changing one or more bits in the memory location from "1" to "0". Thereafter, the expiration date cannot be changed to any later date (unless the correct password is first entered).

Alternatively or additionally, the microcircuit comprising access control circuitry, as described above, may be used to track the number of times the catheter has been used and/or the duration of use, in a manner that is protected from possible tampering or error by a user thereof. Preferably, a record corresponding to the number of times and/or the length of time that the catheter may be used is stored in a memory location in the device or in the microcircuit within the catheter, at the time of manufacture, and the microcircuit is programmed so that this memory location is operable in the "read access and program only" mode, as described above. Each time the catheter is used, and/or at regular time intervals during use, the computer reads the record in the memory location and reduces it by changing one or more bits therein from "1" to "0". When the record stored in the memory location reaches zero, or some other predetermined minimum value, the computer causes a message to be displayed to the user indicating that the catheter is unsuitable for further use and, preferably, prevents further operation until a suitable catheter is connected thereto.

There is therefore provided in accordance with a preferred embodiment of the present invention, a probe assembly for connection to a console including a probe for insertion into the body of a subject, said probe having distal and proximal ends and a microcircuit which stores information relating to the probe and a cable for connecting the probe to the console, said cable including access circuitry for accessing the microcircuit in the probe.

Preferably, the cable is interchangeably connectable to two or more different probes of a common type, and wherein the microcircuit stores information relating uniquely to the probe and substantially not in common with other probes of the type.

Preferably, the access circuitry includes a cable-microcircuit, which stores information relating commonly to different probes of the common type.

Further preferably, the cable-microcircuit stores information identifying the type of the probe.

Preferably, the information relating to the probe includes usage-related information of the probe.

Preferably, the usage related information includes a usage code, which controls availability of the probe to a user thereof.

Preferably, the access circuitry allows the usage code to be changed so as to reduce the availability of the probe, but not to increase the availability thereof.

Preferably, the microcircuit stores the usage code in a memory location therein that is controlled by the access circuitry so as to operate in a read access and program only mode.

Preferably, the mode may be changed by entry of a password to the access circuitry.

Alternatively or additionally, the usage code includes date information.

Preferably, the microcircuit is adjacent to the proximal end of the probe.

Preferably, the microcircuit includes leads which protrude from the proximal end of the probe and wherein the access circuitry includes a socket which receives the leads of the microcircuit.

Preferably, the probe includes a functional portion which generates analog signals and wherein the access circuitry includes one or more amplifiers which amplify the analog signals.

Preferably, the access circuitry includes one or more analog to digital converters.

Preferably, the access circuitry includes a cable-microcircuit, which stores information relating to calibration of the one or more amplifiers.

Alternatively or additionally, the access circuitry includes a cable-microcircuit which stores information relating to the probe assembly.

Preferably, the cable-microcircuit stores information descriptive of a configuration of the probe.

Preferably, the cable-microcircuit stores an allowed usage period for the probe.

Alternatively or additionally, the cable includes an internal clock for measuring the time from a first usage of the catheter.

Preferably, at least a portion of the information on the microcircuit is encrypted.

Preferably, the information relating to the probe includes calibration information of the probe.

Preferably, the probe includes a device that generates signals responsive to the position or orientation of the probe, and the calibration information of the probe includes information relating to calibration of the signal generating device.

Preferably, the signal generating device is adjacent to the distal end of the probe.

Further preferably, the signal generating device includes one or more coils.

Preferably, the calibration information includes information relating to a gain of at least one of the one or more coils.

Alternatively or additionally, the calibration information includes information relating to an angular orientation of at least one of the one or more coils.

Alternatively or additionally, the calibration information includes information relating to a positional displacement of the signal generating device, relative to the distal end of the probe.

Preferably, the probe includes isolation circuitry, and wherein the information relating to the probe includes information relating to a non-linearity of the isolation circuitry.

Preferably, the microcircuit includes a programmable memory device, an EEPROM device, an EPROM or PROM device, a non-volatile RAM device or a Flash ROM device.

Preferably, the cable includes means for disabling at least one of the connections for programming the programmable memory device.

There is further provided in accordance with a preferred embodiment of the present invention, apparatus for determining the position of a probe in the body of a subject, including a probe for insertion into the body of a subject, said probe including a microcircuit which stores calibration information of the probe, a cable for connecting the probe to the console, said cable including access circuitry for accessing the microcircuit in the probe, and a console, including a computer, which receives said position- or orientation-responsive signals and said information relating to calibration and determines therefrom the position of the probe.

Preferably, the probe includes a device that generates signals responsive to the position or orientation of the probe, and the calibration information of the probe includes information relating to calibration of the signal generating device.

Preferably, the microcircuit includes a programmable memory device.

Preferably, the computer is adapted to program the programmable memory device.

There is further provided in accordance with a preferred embodiment of the present invention, a method of initializing a console for use with a probe assembly including a probe and a connection cable, including connecting the probe to the console using the cable, loading the console with general model information from a microcircuit within the cable, and loading the console with specific catheter information from a microcircuit within the catheter.

Preferably, the specific catheter information includes calibration information, a usage code and/or a first usage date.

Preferably, the general information includes a permitted usage duration.

Preferably, the method includes displaying a warning message if the usage duration from the first usage date has expired.

Preferably, connecting the probe to the console includes connecting the probe via access circuitry in the cable.

Preferably, the method includes loading the console with calibration information regarding the access circuitry.

The present invention will be more fully understood from the following detailed description of the preferred embodiments thereof, taken together with the drawings in which:

DETAILED DESCRIPTION OF PREFERRED EMBODIMENTS

Figure 1:
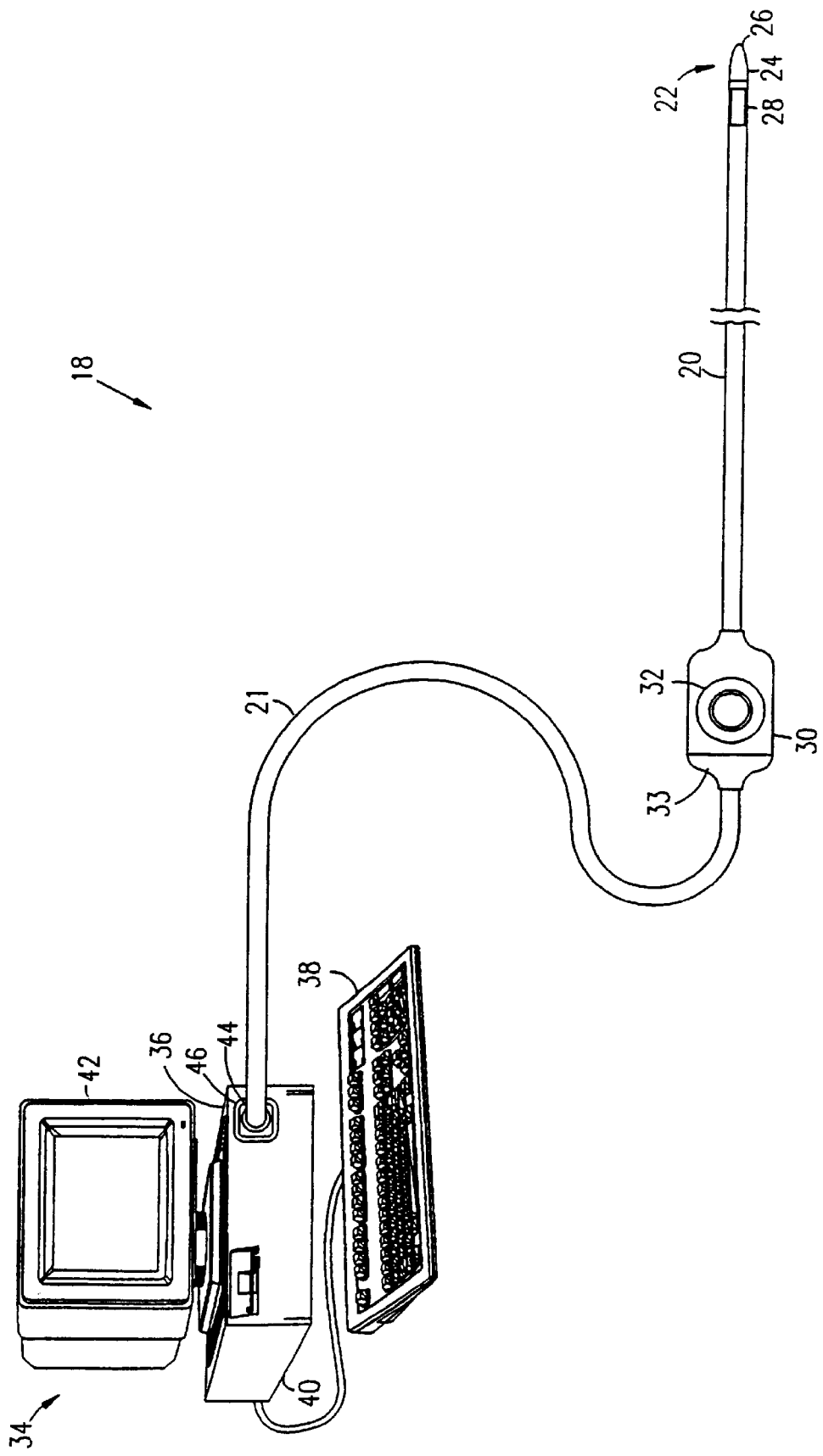
FIG. 1 is a perspective view of a system including a catheter and a connection cable, in accordance with a preferred embodiment of the present invention.

FIG. 1 shows a probe system 18 in accordance with a preferred embodiment of the present invention. System 18 comprises an elongate probe, preferably a catheter 20, for insertion into the human body. It will be understood that although the following preferred embodiments are described with reference to a catheter, the present invention is equally applicable to other types of probes.

A distal end 22 of catheter 20 includes a functional portion 24 for performing diagnostic and/or therapeutic functions, adjacent to distal tip 26. Functional portion 24 may, for example, comprise electrodes (not shown in the figure) for performing electrophysiological measurements or for electrosurgical ablation of areas of pathology in the heart. Alternatively or additionally, the functional portion may comprise other types of sensors, or optical or ultrasound imaging devices.

Distal end 22 of catheter 20 further includes a device 28 that generates signals used to determine the position and orientation of the catheter within the body. Device 28 is preferably adjacent to functional portion 24. There is preferably a fixed positional and orientational relationship between device 28, tip 26 and portion 24.

Catheter 20 preferably includes a handle 30, which includes controls 32 which are used by a surgeon to steer the distal end of the catheter in a desired direction, or to position and/or orient it as desired.

The system shown in FIG. 1 further comprises a console 34, which enables the user to observe and regulate the functions of catheter 20. Console 34 preferably includes a computer 36, keyboard 38, signal processing circuits 40, which are typically inside the computer, and display 42. Signal processing circuits 40 typically receive, amplify, filter and digitize signals from catheter 20, including signals generated by position signal generating device 28, whereupon these digitized signals are received and used by computer 36 to compute the position and orientation of the catheter. Alternatively, appropriate circuitry may be associated with the catheter itself, as described below, so that circuits 40 receive signals that are already amplified, filtered and/or digitized.

Catheter 20 is coupled to computer 36 via an extension cable 21, which at its proximal end comprises a connector 44 adapted to fit in a mating receptacle 46 on console 34. The distal end of cable 21 comprises a receptacle 33 which connects to handle 30. Receptacle 33 is preferably configured to receive catheters of a specific model, and preferably includes user-tangible identification of the specific model. One of the advantages in using cable 21 is the ability to connect different models and types of catheters, possibly having different handle configurations, to the same console 34. Different cables 21 can be used to connect a large variety of catheters to console 34. Another advantage in having a separate cable 21 is in the fact that the cable does not come into contact with patients and therefore it is possible to re-use the cable with sterilization.

Preferably, cable 21 further contains one or more isolation transformers (not shown in the figures), which electrically isolate catheter 20 from console 34. The isolation transformers are preferably contained in receptacle 33.

Figure 2:
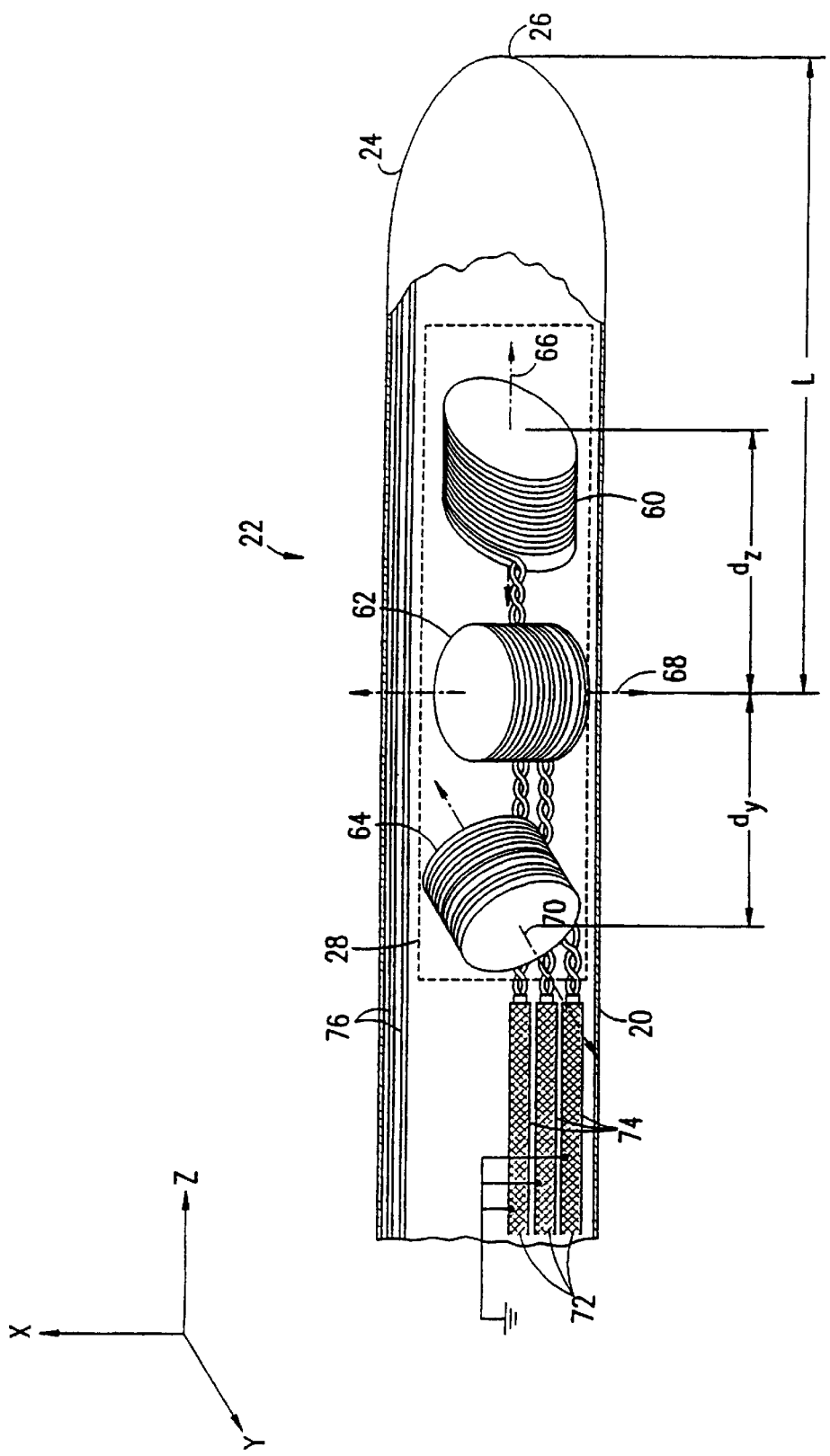
FIG. 2 is a detailed sectional view of the distal end of the catheter of FIG. 1.

Reference is not made to FIG. 2, which shows a detailed view distal end 22 of catheter 20 in accordance with a preferred embodiment of the present invention. Device 28 comprises three non-concentric coils 60, 62 and 64, such as described in PCT patent publication number WO96/05768, whose disclosure is incorporated herein by reference. This device enables continuous generation of six dimensions of position and orientation information with respect to an externally-applied magnetic field. Coils 60, 62 and 64 have respective axes 66, 68 and 70, which preferably define orthogonal Cartesian axes Z, X and Y, respectively, as shown in FIG. 2, wherein the Z-axis is parallel to the long axis of catheter 20 and the X- and Y-axes define a plane perpendicular thereto. The coils each have a fixed position and orientation with respect to each other.

Although preferred embodiments of the present invention are described herein with reference to position signal generating device 28 shown in FIG. 2 and described above, it will be understood that the inventive concepts of the present invention are similarly applicable to probes including other position sensing devices. For example, in other preferred embodiments of the present invention, the probe may comprise a single coil for generating position signals, or two or more such coils, which may be concentric or non-concentric. Other preferred embodiments of the present invention may comprise other types of position sensing devices known in the art, such as Hall effect devices or ultrasonic or optical sensors.

As shown in FIG. 2, device 28 is located in catheter 20 at a distance L from distal tip 26, where L is herein defined for convenience as the distance along the Z-axis from the central axis 68 of coil 26 to tip 26. Respective axes 66 and 70 of coils 60 and 64 are displaced from axis 68 by respective distances $d_y$ and $d_z$.

When a time-varying external magnetic field is applied to distal end 22 of catheter 20, coils 60, 62 and 64 generate analog signals, which are preferably conveyed through the catheter by coil wires 72. The amplitudes of these analog signals are typically small relative to other electrical signals in and around catheter 20, such as the electrophysiological signals measured by functional portion 24 and conveyed through the catheter by functional wires 76. Furthermore, external magnetic fields may also cause undesired electrical currents, not generated by coils 60, 62 and 64, to flow in coil wires 72. These other electrical signals and undesired electrical currents can cause noise or interference signals to appear together with the signals generated by the coils. Therefore, in preferred embodiments of the present invention, wires 72 are configured as twisted pairs and may also be shielded from electromagnetic interference by shield 74, so as to maintain a high signal-to-noise ratio in the position and orientation signals received from the coils.

As described in the above-mentioned 05768 PCT patent publication, signal processing circuits 40 in console 34 receive the signals carried by coil wires 72 and convey them to computer 36, which computes the three-dimensional translational position of device 28 and the rotational orientation of axes 66, 68 and 70, relative to a fixed, external coordinate frame. The actual position and orientation of distal tip 26 are then computed by taking into account the distance L of tip 26 from the center of device 28, as defined by axis 68, and the orientation of axes 66, 68 and 70.

It has been found empirically that due to deviations in the process of manufacturing catheter 20, the distance L typically varies from one catheter to another, leading to errors in calculating the position of tip 26. Furthermore, axis 66 of coil 60 typically deviates from absolute alignment with the long axis of catheter 20, which passes through tip 26, and axes 68 and 70 of coils 62 and 64 respectively are typically not precisely orthogonal to axis 66 or to each other, thereby inducing additional errors in determination of position and orientation of the catheter. Finally, variations in the respective gains of coils 60, 62 and 64 and in the distances $d_y$ and $d_z$ may cause additional errors in determination of position and orientation of the catheter.

Therefore, in preferred embodiments of the present invention, device 28 that is used to determine the position and orientation of catheter 20 is calibrated before the catheter is inserted into a patient's body. This calibration may be performed using any suitable method including the methods described in PCT/IL97/00060. The determined calibration correction function is thereafter stored electronically in a memory device, which device is preferably in catheter 20. When the catheter is coupled to console 34, this memory device is accessible to computer 36 in the console.

Figure 3:
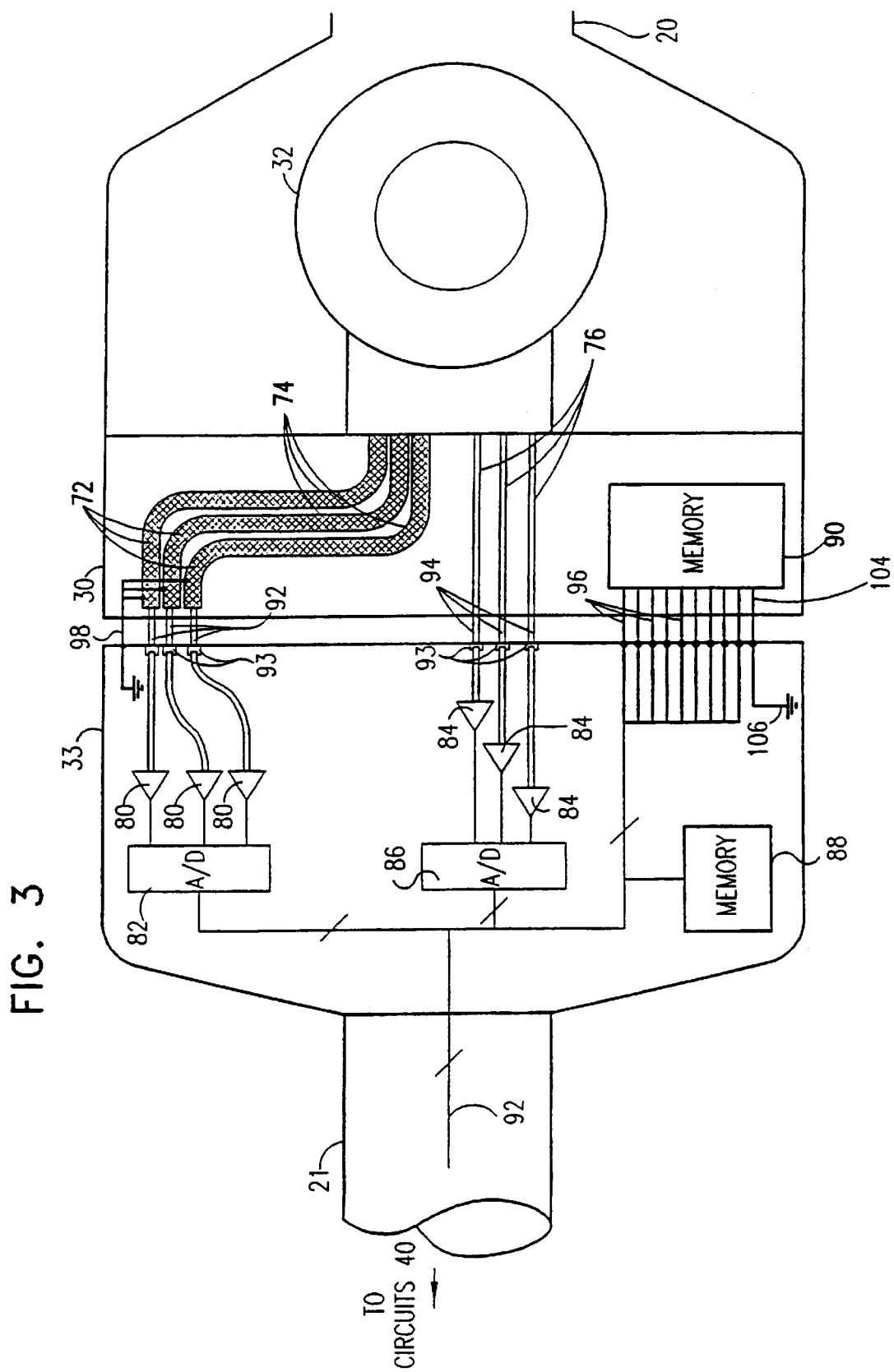
FIG. 3 is a detailed schematic view of a connection site between the catheter and the cable, in accordance with a preferred embodiment of the present invention.

FIG. 3 shows details of receptacle 33 and handle 30, in accordance with a preferred embodiment of the present invention. Handle 30 includes a digital microcircuit 90 in which calibration data for catheter 20 are electronically stored. Microcircuit 90 preferably includes an EEPROM or Flash ROM, but may alternatively include EPROM, PROM non-volatile RAM, or other types of programmable memory devices known in the art. When a catheter 20 is calibrated, its specific calibration data are stored in microcircuit 90 and thus the data is conveniently accessible to computer 36, as will be described above.

Preferably, another microcircuit 88 is included in receptacle 33 of cable 21. Microcircuit 88 preferably includes a programmable memory similar to that of microcircuit 90. Information regarding initialization of catheter 20 which is common to all catheters of a certain model is preferably stored in microcircuit 88 rather than in microcircuit 90, which is embedded within the catheter itself. Most catheters are limited in the number of times they may be used, because of problems of cleaning, sterilization and wear. Commonly catheters may be used only once. Therefore, it is desirable to minimize the cost of the catheter itself by incorporating into catheter 20 only the minimal circuitry necessary, including a minimal size microcircuit 90. All other information which is characteristic commonly of all catheters of a given model is stored within receptacle 33, which is not inserted into the patient's body. Alternatively or additionally, information characteristic of a family of catheters is stored within console 36 while cable 21 only holds minimal information identifying which catheter model is being used.

An advantage of having the model information in receptacle 33 rather than in console 36 lies in allowing use of a large variety of catheter with console 36 without loading large databases into the consoles. Furthermore, microcircuit 88 preferably stores calibration information relating to circuitry in the receptacle, as described below. These features allow using a standard console with various catheter types, rather than having a single console 36 associated with each type of catheter. Furthermore, newer models of catheters may be used with console 36 simply by connecting them via their compatible cable 21 to the console, thus reducing the need to update software in the console or to acquire a new console.

In the preferred embodiment shown in FIG. 3, handle 30 further includes pins 92, 94, 96 and 98, which mate with corresponding sockets 93 in receptacle 33. Functional pins 94 couple analog electrophysiological signals conveyed over functional wires 76 to signal processing circuits 40. Coil pins 92 couple analog position and orientation signals conveyed by coil wires 72 from coils 60, 62 and 64 to signal processing circuits 40 and computer 36, which compute the position and orientation of catheter 20. The computer further reads the digital calibration correction data stored in microcircuit 90 via memory pin 96, and uses these data in computing the correct catheter position and orientation.

Receptacle 33 preferably comprises one or more amplifiers 80 which amplify the position and orientation signals conveyed by coil wires 72. These signals are generally very weak, and therefore it is important to locate amplifiers 80 as close as possible to coils 60, 62, and 64 which produce the signals. However, it is advantageous not to locate amplifiers 80 within catheter 20 since they increase the cost the complexity of the catheter unduly. Preferably, receptacle 33 further comprises one or more analog-to-digital (A/D) converters 82 which convert the analog signals from amplifiers 80 to digital form.

Preferably, the physiological signals conveyed over functional wires 76 are also amplified by amplifiers 84 and are then converted to digital form via A/D converter 86. Preferably, calibration information for amplifiers 80 and 84, such as gain and offset, is stored in microcircuit 88.

One or more write-enable pins 104 are preferably coupled to microcircuit 90. These pins are used to enable programming of the microcircuit with the desired calibration data. At the time of calibration, the write-enable input is enabled, and calibration data are recorded in the microcircuit. Thereafter the write-enable input is disabled, for example by removing the write-enable pin or by connecting it to electrical ground 106, as shown in FIG. 3, so that further calibration data may not be recorded in the microcircuit, and the microcircuit functions in a read-only mode. Microcircuit 88 may be programmed in like fashion.

Alternatively, in preferred embodiments of the present invention wherein microcircuit 90 comprises an EEPROM device, the write-enable input may be disabled by sending a write-protect command to the device. This command may be reversible or irreversible.

In other preferred embodiments of the present invention, microcircuit 90 comprises a device incorporating password-secured access control, and write-access to the microcircuit requires that an appropriate password first be entered. For example, in one such preferred embodiment, microcircuit 90 comprises a Password Access Security Supervisor (PASS™) X76F041 SecureFlash ROM device, manufactured by Xicor, Inc. The microcircuit is programmed with calibration data at the time of manufacture, and thereafter operates in a "read access only" mode, with all write operations locks out, or in a "read access and program only" mode, in which certain data, but not calibration data, may be written to the device, as will be described below. Changing the mode of operation of the microcircuit requires that an appropriate password be entered, which password is generally unavailable to users of the system.

In another embodiment of the present invention, microcircuit 90 comprises an EPROM or PROM. Calibration data are recorded in the EPROM or PROM at the time of manufacture using a suitable programming device, not shown in the figures, which receives data from the computer used in calibration. The programming device is connected to handle 30 via a calibration socket, not shown in the figures, which like receptacle 33 is adapted to receive handle 30. The programming device programs the EPROM or PROM by inputting digital signals thereto through the connector. Thereafter, the EPROM or PROM may not be re-programmed.

In some preferred embodiment of the present invention, data recorded in microcircuit 90 and/or microcircuit 88 include a calibration code, which is encrypted in accordance with methods known in the art, so as to ensure that the calibration data have not been altered or corrupted. Preferably the calibration code includes a checksum. When the user connects catheter 20 to console 34, computer 36 reads the calibration code and compares the code with preprogrammed values. If the code does not match the desired pre-programmed value, the computer causes a message to be displayed by display 42 indicating that the catheter may not be appropriately calibrated. The computer may further cause the system to cease operation until a catheter having a code matching the desired pre-programmed value is connected thereto.

Preferably the calibration code is encrypted using a method that prevents decryption by unauthorized parties, for example the RSA encryption scheme, using a public key and a private key, or other methods known in the art. When a method such as RSA encryption is used, the private key is known only to authorized manufacturers of the catheter, so as to prevent the possible use of unauthorized substitutes of possibly inferior quality.

In further preferred embodiments of the present invention, data recorded in microcircuit 90 include an expiration date and time, after which the catheter may not be used. Microcircuit 88 may similarly include data relating to the maximal period over which the catheter may be used. When a user connects catheter 20 to a console 34, computer 36 reads the expiration date and time and compares them to the actual date and time, generated, for example, by a real-time clock circuit. If the expiration date and time have passed, the computer causes a message to be displayed by display 42 indicating that the catheter is unsuitable for further use. Alternatively or additionally, the computer may prevent usage of catheter 20 after the expiration date.

In a preferred embodiment of the present invention, cable 21 includes an internal clock which keeps track of the time and date. Alternatively or additionally, the internal clock of cable 21 keeps track of the relative time from the first use of catheter 20. Thus, it is not possible to avoid the usage prevention by changing the date in the console.

Preferably the expiration date and time are recorded by computer 36 by programming microcircuit 90 when catheter 20 is first used. When catheter 20 is connected to console 34 for the first time, computer 36 detects that no expiration date and time have yet been recorded in microcircuit 90, and programs the microcircuit with the appropriate expiration date and time, at a pre-set interval after the current date and time. The pre-set interval is preferably determined by the manufacturer, based on the expected useful life of the catheter.

In preferred embodiments of the present invention in which microcircuit 90 comprises a device including access control circuitry, such as the aforementioned X76F041 device, the microcircuit is programmed so that a memory location therein is operable in a "read access and program only" mode. The mode may be changed only by entry of an appropriate password, which is generally not available to users of the system. In the "read access and program only" mode, a number stored in the memory location may be decreased, by changing a bit from "1" to "0", but not increased, since the microcircuit as programmed will not permit a "0" to be changed to a "1". Preferably the memory location is set at the time of manufacture to contain a maximum value, i.e., all bits set to "1". Then, as described above, at the time catheter 20 is first used, computer 36 programs the microcircuit with the appropriate expiration time and date by changing one or more bits in the memory location from "1" to "0". Thereafter, the expiration date cannot be changed to any late date (unless the correct password is first entered).

Alternatively or additionally, microcircuit 90 comprising access control circuitry, as described above, may be used to track the number of times catheter 20 has been used, in a manner that is protected from possible tampering or error by a user thereof. Preferably, a record corresponding to the number of times catheter 20 may be used is stored in a memory location in the device at the time of manufacture, and the microcircuit is programmed so that this memory location is operable in the "read access and program only" mode, as described above. Each time the catheter is used, computer 36 reads the record in the memory location and reduces it by changing one or more bits therein from "1" to "0". When all the bits in the record are equal to zero, or the record reaches some other predetermined minimum value, the computer causes a message to be displayed to the user indicating that the catheter is unsuitable for further use and, preferably, prevents further operation until a suitable catheter is connected thereto.

Similarly, either alternatively or additionally, microcircuit 90 may be used to track the duration of use of catheter 20. In this case, a record corresponding to the duration of use of the catheter is stored in a "read access and program only" memory location in the microcircuit. While the catheter is in use, at regular, predetermined intervals, computer 36 reads the record and reduces it by changing one or more bits therein from "1" to "0". When the entire record reaches zero, or some other minimum value, further operation is prevented, as described above. As noted earlier, the low-level analog signals conveyed from coils 60, 62 and 64 over coil wires 72 must generally be protected from interference due to other analog signals in functional wires 76 and digital signals conveyed to an from microcircuit 90. Therefore, in preferred embodiments of the present invention, as shown in FIG. 3, handle 30 includes electromagnetic shields 74, which are coupled to ground via pin 98 on the connector.

In another preferred embodiment of the present invention, shields 74 are active shields, which are driven by noise canceling circuitry (not shown).

Although most of the features and capabilities of system 18, particularly features related to access control, have been described above with reference to microcircuit 90 in catheter handle 30, it will be clear to those skilled in the art that many of these features and capabilities could be implemented using microcircuit 88 in cable 21, as well.

Furthermore, although the above preferred embodiments have been described with reference to calibration of position and orientation sensing apparatus, in other preferred embodiments of the present invention, calibration data stored in catheter 20, and specifically in microcircuits 88 and 90, may relate to other aspects of the catheter. For example, in some preferred embodiments of the present invention, calibration data relating to a physiological sensor, actuator or therapeutic tool are stored in the catheter. In another preferred embodiment of the present invention, calibration data may be stored in the catheter regarding the gain of a piezoelectric motion control device used in steering the catheter's distal end.

It will be appreciated that the preferred embodiments of the invention described above are cited by way of example, and the full scope of the invention is limited only by the claims which follow.

What is claimed is:

1. A probe assembly for connection to a console comprising:
    a probe for insertion into the body of a subject, said probe having distal and proximal ends and comprising a microcircuit which stores information relating to the probe, wherein the information relating to the probe comprises usage-related information of the probe and the usage related information comprises a usage code, which controls availability of the probe to a user thereof; and
    a cable for connecting the probe to the console, said cable comprising access circuitry for accessing the microcircuit in the probe.

2. An assembly in accordance with claim 1, wherein the cable is interchangeably connectable to two or more different probes of a common type, and wherein the microcircuit stores information relating uniquely to the probe and substantially not in common with other probes of the type.

3. An assembly according to claim 2, wherein the access circuitry comprises a cable-microcircuit, which stores information relating commonly to different probes of the common type.

4. An assembly according to claim 3, wherein the cable-microcircuit stores information identifying the type of the probe.

5. An assembly in accordance with claim 1 wherein the access circuitry allows the usage code to be changed so as to reduce the availability of the probe, but not to increase the availability thereof.

6. An assembly in accordance with claim 1, wherein the microcircuit stores the usage code in a memory location therein that is controlled by the access circuitry so as to operate in a read access and program only mode.

7. An assembly in accordance with claim 6, wherein the mode may be changed by entry of a password to the access circuitry.

8. An assembly in accordance with claim 7, wherein the usage code includes date information.

9. An assembly in accordance with claim 1, wherein the microcircuit is adjacent to the proximal end of the probe.

10. An assembly in accordance with claim 9, wherein the microcircuit comprises leads which protrude from the proximal end of the probe and wherein the access circuitry comprises a socket which receives the leads of the microcircuit.

11. An assembly in accordance with claim 1, wherein the probe comprises a functional portion which generates analog signals and wherein the access circuitry comprises one or more amplifiers which amplify the analog signals.

12. An assembly in accordance with claim 11, wherein the access circuitry comprises one or more analog to digital converters.

13. An assembly in accordance with claim 11, wherein the access circuitry comprise a cable-microcircuit, which stores information relating to calibration of the one or more amplifiers.

14. An assembly in accordance with claim 1, wherein the access circuitry comprises a cable-microcircuit which stores information relating to the probe assembly.

15. An assembly in accordance with claim 14, wherein the cable-microcircuit stores information descriptive of a configuration of the probe.

16. An assembly in accordance with claim 14, wherein the cable-microcircuit stores an allowed usage period for the probe.

17. An assembly in accordance with claim 1, wherein the cable comprises an internal clock for measuring the time from a first usage of the catheter.

18. An assembly in accordance with claim 1, wherein at least a portion of the information on the microcircuit is encrypted.

19. An assembly in accordance with claim 1, wherein the information relating to the probe comprises calibration information of the probe.

20. An assembly in accordance with claim 19, wherein the probe comprises a device that generates signals responsive to the position or orientation of the probe, and the calibration information of the probe comprises information relating to calibrate of the signal generating device.

21. An assembly in accordance with claim 20, wherein said signal generating device is adjacent to the distal end of the probe.

22. An assembly in accordance with claim 20, wherein the signal generating device comprises one or more coils.

23. An assembly in accordance with claim 22, wherein the calibration information comprises information relating to a gain of at least one of the one or more coils.

24. An assembly in accordance with claim 22, wherein the calibration information comprises information relating to an angular orientation of at least one of the one or more coils.

25. An assembly in accordance with claim 20, wherein the calibration information comprises information relating to a positional displacement of the signal generating device, relative to the distal end of the probe.

26. An assembly in accordance with claim 1, wherein the probe includes isolation circuitry, and wherein the information relating to the probe comprises information relating to a non-linearity of the isolation circuitry.

27. An assembly in accordance with claim 1, wherein the microcircuit comprises a programmable memory device.

28. A probe in accordance with claim 27, wherein the programmable memory device comprises an EEPROM device.

29. A probe in accordance with claim 27, wherein the programmable memory device comprises an EPROM or PROM device.

30. A probe in accordance with claim 27, wherein the programmable memory device comprises a Flash ROM device.

31. Apparatus in accordance with claim 27, wherein the cable includes means for disabling at least one of the connection for programming the programmable memory device.

32. Apparatus for determining the position of a probe in the body of a subject, comprising:

a probe for insertion into the body of a subject, said probe comprising a microcircuit which stores calibration information of the probe, said probe generating position or orientation responsive signals;

a cable for connecting the probe to the console, said cable comprising access circuitry for accessing the microcircuit in the probe; and a console, comprising a computer, which receives said position or orientation responsive signals and said information relating to calibration and determines therefrom the position of the probe.

33. An assembly in accordance with claim 32, wherein the probe comprises a device that generates signals responsive to the position or orientation of the probe, and the calibration information of the probe comprises information relating to calibration of the signal generating device.

34. Apparatus in accordance with claim 33, wherein the microcircuit comprises a programmable memory device.

35. Apparatus in accordance with claim 34, wherein the computer is adapted to program the programmable memory device.

36. A method of initializing a console for use with a probe assembly including a probe and a connection cable, comprising:

connecting the probe to the console using the cable;

loading the console with general model information from a microcircuit within the cable; and loading the console with specific probe information from a microcircuit within the probe wherein the specific probe information comprises calibration information.

37. A method in accordance with claim 36, wherein the specific probe information comprises a usage code.

38. A method in accordance with claim 36, wherein the specific probe information comprises a first usage data.

39. A method in accordance with claim 38, wherein the general model information comprises a permitted usage duration.

40. A method in accordance with claim 39, and comprising displaying a warning message if the usage duration from the first usage date has expired.

41. A method in accordance with claim 40, wherein connecting the probe to the console comprises connecting the probe via access circuitry in the cable.

42. A method in accordance with claim 41, and comprising loading the console with calibration information regarding the access circuitry.

* * * * *